(12) United States Patent
Zunker

(10) Patent No.: US 6,458,072 B1
(45) Date of Patent: Oct. 1, 2002

(54) URINARY INCONTINENCE DEVICE

(75) Inventor: MaryAnn Zunker, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/838,600

(22) Filed: Apr. 19, 2001

(51) Int. Cl.$^7$ ............................................. A61M 31/00
(52) U.S. Cl. ........................................................ 600/29
(58) Field of Search ........................................... 600/29

(56) References Cited

U.S. PATENT DOCUMENTS

| | | |
|---|---|---|
| 3,726,277 A | 4/1973 | Hirschman |
| 3,762,414 A | 10/1973 | Burnhill |
| 3,780,730 A | 12/1973 | Weisman |
| 3,834,389 A | 9/1974 | Dulle |
| 3,902,493 A | 9/1975 | Baier et al. |
| 3,971,378 A | 7/1976 | Krantz |
| 3,981,305 A | 9/1976 | Ring |
| 3,999,549 A | 12/1976 | Poncy et al. |
| 4,019,498 A | 4/1977 | Hawtrey et al. |
| 4,020,841 A | 5/1977 | Poncy et al. |
| 4,108,180 A | 8/1978 | Moehrle |
| 4,139,006 A | 2/1979 | Corey |
| 4,175,561 A | 11/1979 | Hirschman |
| 4,185,631 A | 1/1980 | McConnell |
| 4,351,338 A | 9/1982 | Langlois et al. |
| 4,516,570 A | 5/1985 | Taban |
| 4,601,714 A | 7/1986 | Burnhill |
| 4,669,478 A | 6/1987 | Robertson |
| 4,681,572 A | 7/1987 | Tokarz et al. |
| 4,823,814 A | 4/1989 | Drogendijk et al. |
| 4,875,898 A | 10/1989 | Eakin |
| 4,920,986 A | 5/1990 | Biswas |
| 4,922,928 A | 5/1990 | Burnhill |
| 4,969,474 A | 11/1990 | Schwarz |
| 5,007,894 A | 4/1991 | Enhorning |
| 5,036,867 A | 8/1991 | Biswas |
| 5,045,079 A | 9/1991 | West |
| 5,074,855 A | 12/1991 | Rosenbluth et al. |
| 5,090,424 A | 2/1992 | Simon et al. |
| 5,224,494 A | 7/1993 | Enhorning |
| 5,299,581 A | 4/1994 | Donnell et al. |
| 5,334,216 A | 8/1994 | Vidal et al. |
| 5,336,208 A | 8/1994 | Rosenbluth et al. |
| 5,355,896 A | 10/1994 | Schulman |
| 5,374,261 A | 12/1994 | Yoon |
| 5,386,836 A | 2/1995 | Biswas |
| 5,417,224 A | 5/1995 | Petrus et al. |
| 5,483,976 A | 1/1996 | McLaughlin et al. |
| 5,512,032 A | 4/1996 | Kulisz et al. |
| 5,527,534 A | 6/1996 | Myhling |

(List continued on next page.)

FOREIGN PATENT DOCUMENTS

| | | |
|---|---|---|
| DE | 19602878 C1 | 9/1997 |
| EP | 0 363 421 B2 | 10/1995 |
| WO | WO 95/28139 A1 | 10/1995 |
| WO | WO 98/34677 A1 | 8/1998 |
| WO | WO 00/67662 A1 | 11/2000 |

*Primary Examiner*—Gerald A. Michalsky
(74) *Attorney, Agent, or Firm*—Thomas J. Connelly

(57) ABSTRACT

A urinary incontinence device is disclosed which includes a first absorbent and a second absorbent. The first absorbent has a width and the second absorbent is positioned adjacent to the first absorbent. The second absorbent has a width that is less than about 80% of the width of the first absorbent. The first and second absorbents are formed into a softwind that is compressed into an elongated pledget having a cross-sectional area. The first and second absorbents are capable of absorbing fluid and expanding the cross-sectional area of the pledget. The second absorbent causing a portion of the cross-sectional area of the pledget to expand farther outward to provide a supportive backdrop for a woman's urethra when inserted into a woman's vagina.

20 Claims, 6 Drawing Sheets

U.S. PATENT DOCUMENTS

| | | |
|---|---|---|
| 5,609,586 A | 3/1997 | Zadini et al. |
| 5,618,256 A | 4/1997 | Reimer |
| 5,659,934 A | 8/1997 | Jessup et al. |
| 5,755,236 A | 5/1998 | Dann et al. |
| 5,755,906 A | 5/1998 | Achter et al. |
| 5,785,640 A | 7/1998 | Kresch et al. |
| 5,795,346 A | 8/1998 | Achter et al. |
| 5,988,169 A | 11/1999 | Anderson et al. |
| 6,039,716 A | 3/2000 | Jessup et al. |
| 6,039,828 A | 3/2000 | Achter et al. |
| 6,090,038 A | 7/2000 | Zunker et al. |
| 6,090,098 A | 7/2000 | Zunker et al. |
| 6,142,928 A | 11/2000 | Zunker et al. |

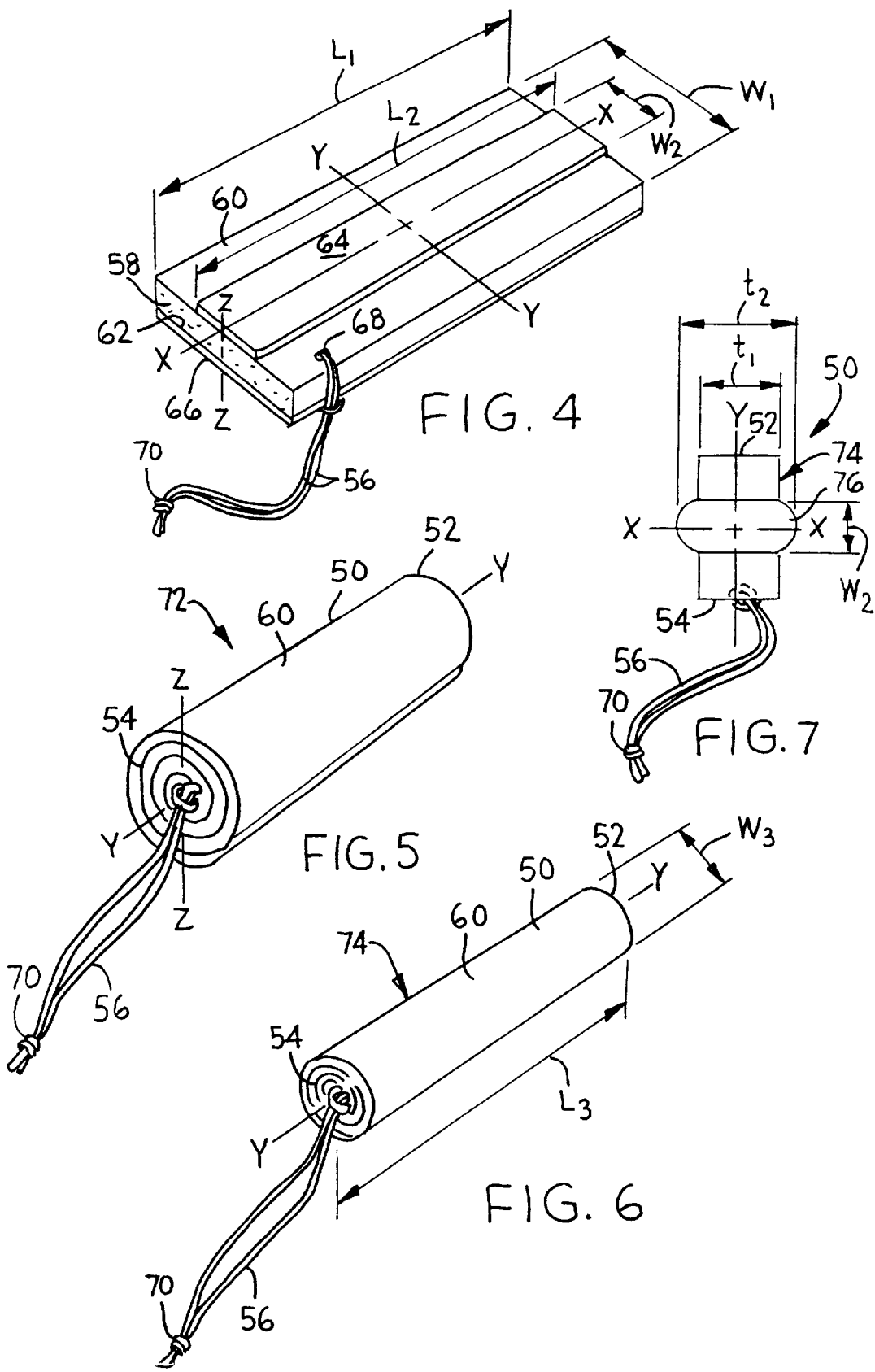

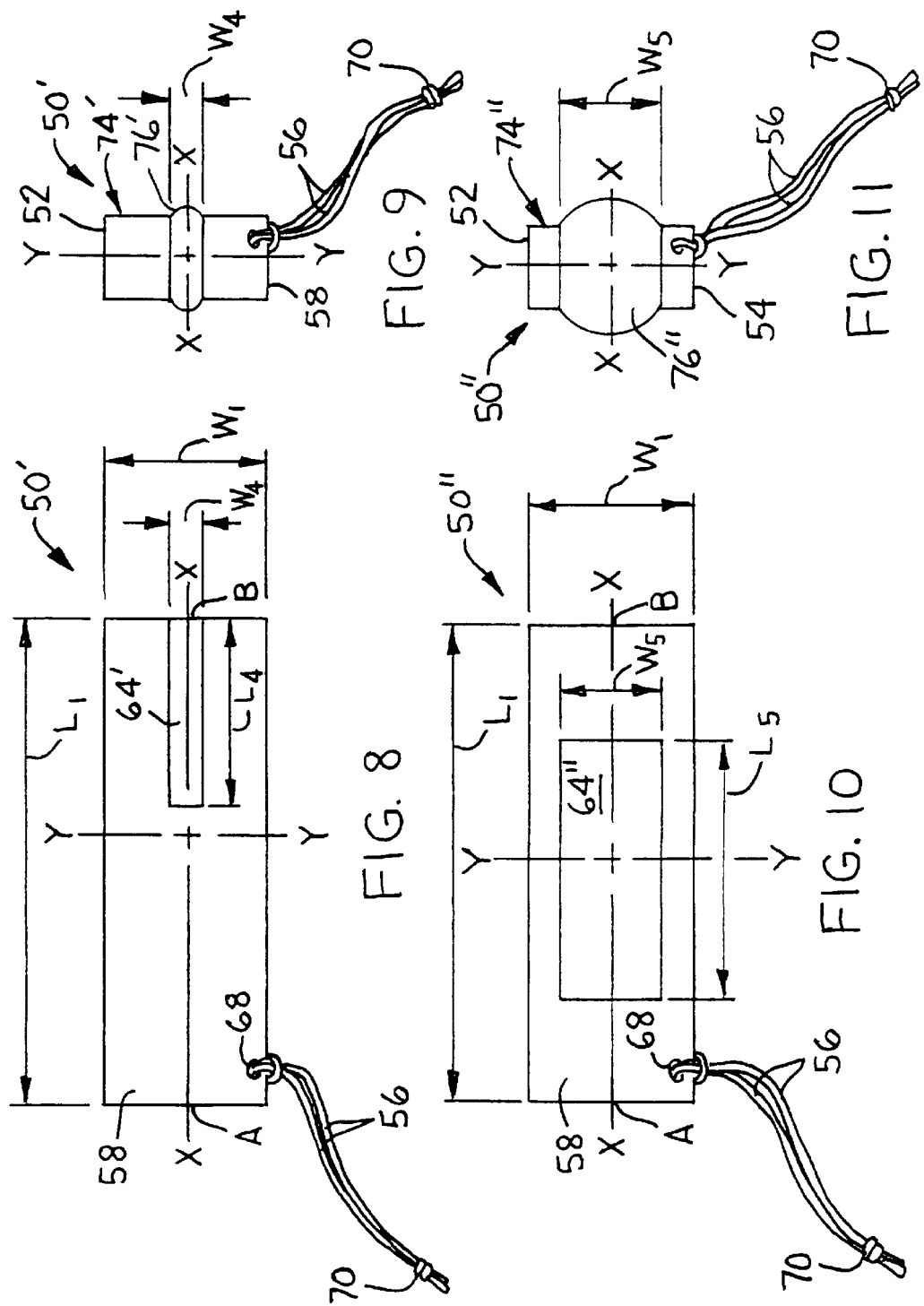

```
┌─────────────────────────────────────────────────┐
│   PROVIDING A URINARY INCONTINENCE DEVICE       │
│      WITH FIRST AND SECOND ABSORBENTS           │
└─────────────────────────────────────────────────┘
                        │
┌─────────────────────────────────────────────────┐
│   INSERTING SAID DEVICE INTO A WOMAN'S VAGINA   │
└─────────────────────────────────────────────────┘
                        │
┌─────────────────────────────────────────────────┐
│  POSITIONING SAID DEVICE IN THE UPPER 2/3 OF THE│
│          LENGTH OF THE VAGINAL CANAL            │
└─────────────────────────────────────────────────┘
                        │
┌─────────────────────────────────────────────────┐
│   ALLOWING SAID FIRST AND SECOND ABSORBENTS     │
│           TO EXPAND RADIALLY OUTWARD            │
└─────────────────────────────────────────────────┘
                        │
┌─────────────────────────────────────────────────┐
│  PERMITTING THE WOMAN'S URETHRAL TUBE TO BE     │
│            COMPRESSED UPON ITSELF               │
└─────────────────────────────────────────────────┘
```

FIG. 17

```
┌─────────────────────────────────────────────────┐
│   PROVIDING A URINARY INCONTINENCE DEVICE       │
│   WITH FIRST AND SECOND ABSORBENTS              │
└─────────────────────────────────────────────────┘
                         │
┌─────────────────────────────────────────────────┐
│   INSERTING SAID DEVICE INTO A WOMAN'S VAGINA   │
└─────────────────────────────────────────────────┘
                         │
┌─────────────────────────────────────────────────┐
│   POSITIONING SAID DEVICE IN THE UPPER 2/3 OF THE│
│   LENGTH OF THE VAGINAL CANAL                   │
└─────────────────────────────────────────────────┘
                         │
┌─────────────────────────────────────────────────┐
│   ALLOWING SAID FIRST AND SECOND ABSORBENTS     │
│   TO EXPAND RADIALLY OUTWARD                    │
└─────────────────────────────────────────────────┘
                         │
┌─────────────────────────────────────────────────┐
│   PERMITTING THE WOMAN'S URETHRAL TUBE TO BE    │
│   COMPRESSED UPON ITSELF                        │
└─────────────────────────────────────────────────┘
                         │
┌─────────────────────────────────────────────────┐
│   REMOVING THE DEVICE FROM THE WOMAN'S VAGINA   │
└─────────────────────────────────────────────────┘
```

FIG. 18

URINARY INCONTINENCE DEVICE

FIELD OF THE INVENTION

This invention relates to a urinary incontinence device for alleviating female urinary incontinence. More specifically, this invention relates to a urinary incontinence device for alleviating female urinary incontinence during episodes of increased intra-abdominal pressure.

BACKGROUND OF THE INVENTION

The primary etiological factor producing genuine stress urinary incontinence is the incomplete transmission of abdominal pressure to the proximal urethra due to displacement from its intra-abdominal position. Some women, especially women who have given birth to one or more children, and older women, can experience incidences of involuntary urine loss due to stress urinary incontinence or combined stress and urge incontinence. A sneeze or cough can increase the intra-abdominal pressure impinging on a person's bladder thereby causing the involuntary release of urine. The frequency and severity of such urine loss can increase as the muscles and tissues, particularly near the urethro-vaginal myofascial area, grow weaker. It has also been recognized that the urinary sphincter muscle, which is located at the upper end of the urethra, adjacent to the bladder, works well at sealing off the passing of urine from the bladder to the urethra when it has a generally round or circular cross-sectional configuration. Support of the proximal urethra elevates it above the pelvic floor and subjects it to increases in intra-abdominal pressure, thus allowing compression and maintenance of continence. However, when this passageway becomes distorted into a cross-sectional configuration having more of an elliptical or oval appearance, the sphincter muscle can not close properly, therefore, the tendency for involuntary urine loss increases. One must remember that the urethra and vagina are not separate structures. Because of their common derivation from the urogenital sinus, they are fused in the distal two thirds of the urethra. In this region, they are bound together by the endopelvic connective tissue so that the support of the urethra depends not only on the attachments of the urethra itself to adjacent structures but also on the connection of the vagina and periurethral tissues to the pelvic wall.

As the world's female population ages, there is an ever-increasing need for a non-surgical method or measure to reduce the involuntary urine loss commonly associated with stress urinary incontinence. Today, there are a number of specialized products available for this purpose. Most of these products can only be purchased with a prescription and they need to be properly sized, physically inserted and/or adjusted by a medical doctor or a nurse practitioner in order to perform correctly. Few, if any, products are commercially available in the United States, without a prescription, to prevent the involuntary urine loss associated with stress urinary incontinence.

In view of the lack of commercially available, non-prescription urinary incontinence prevention or mitigation devices, it is recognized that there is a need for a urinary incontinence device that can be purchased without a prescription. There is also a need for a urinary incontinence device that is uncomplicated and therefore more user friendly and can be managed by the consumer without the intervention of a medical practitioner. Furthermore, there is a need for a urinary incontinence device which is easy for women to insert into and remove from their bodies, be more comfortable to wear and provide psychological and realistic assurance that it is capable of properly performing over an extended period of time.

SUMMARY OF THE INVENTION

Briefly, this invention relates to a urinary incontinence device for alleviating female urinary incontinence. The urinary incontinence device includes a first absorbent and a second absorbent. The first absorbent has a width and a longitudinal axis. The second absorbent is positioned adjacent to the first absorbent and is aligned along the longitudinal axis. The second absorbent has a width that is less than about 80% of the width of the first absorbent. The first and second absorbents are formed into a softwind that is compressed into an elongated pledget having a cross-sectional area. The first and second absorbents are capable of absorbing fluid and expanding the cross-sectional area of the pledget. The second absorbent causes a portion of the cross-sectional area of the pledget to expand farther outward to provide a supportive backdrop for a woman's urethra when inserted into a woman's vagina.

The urinary incontinence device is inserted into a woman's vagina with the insertion end entering first. The vagina has a vaginal canal with an inner periphery made up of right and left lateral walls, an anterior wall and a posterior wall. The urinary incontinence device is sized to contact at least two of the walls when inserted into the vagina. The urinary incontinence device is positioned in a middle third of the length of the vaginal canal with the insertion end aligned nearly adjacent to a woman's urethral sphincter muscle, which is a part of a woman's urethral tube. The urinary incontinence device cooperates with a woman's symphysis pubis to compress the urethral tube therebetween. The urinary incontinence device is allowed to expand within the vaginal canal upon absorbing body fluid. As the urinary incontinence device expands, at least a portion of it increases in cross-sectional area and contacts all four interior walls of the vaginal canal and provides a supportive backdrop for the urethral tube. The urethral tube can then be compressed upon itself between the urinary incontinence device and the symphysis pubis thereby limiting involuntary urine flow.

The general object of this invention is to provide a urinary incontinence device for alleviating female urinary incontinence. More specifically, this invention relates to a urinary incontinence device for alleviating female urinary incontinence during episodes of increased intra-abdominal pressure.

A more specific object of this invention is to provide a urinary incontinence device that is placed in a woman's vagina and allows for transmission of pressure sufficient to allow the urethra to collapse upon itself to prevent or mitigate involuntary urine loss commonly associated with stress urinary incontinence.

Another object of this invention is to provide a urinary incontinence device that is simple to use, easy to insert and remove, and which is comfortable to wear.

A further object of this invention is to provide a urinary incontinence device that can be manufactured and sold for a reasonable cost.

Still another object of this invention is to provide a urinary incontinence device that can be purchased by a consumer without a prescription.

Still further, an object of this invention is to provide a urinary incontinence device that does not disrupt the normal vaginal micro-flora which are necessary for a healthy vaginal environment.

Other objects and advantages of the present invention will become more apparent to those skilled in the art in view of the following description and the accompanying drawings.

BRIEF DESCRIPTION OF THE DRAWINGS

FIG. 4 is a perspective view of the urinary incontinence device including a cover and a withdrawal string.

FIG. 5 is a perspective view of the first and second absorbents and the cover after being radially wound along the longitudinal axis x—x to form a softwind.

FIG. 6 is a perspective view of an elongated pledget formed by radially compressing the softwind depicted in FIG. 5.

FIG. 7 is a side view of the urinary incontinence device depicted in FIG. 6 when in an expanded state after absorbing fluid showing the outward bulge caused by the expansion of the first and second absorbents.

FIG. 8 is a top view of an alternative embodiment of the urinary incontinence device showing the second absorbent having a length that is less than 50% of the length of the first absorbent and a width that is less than 35% of the width of the first absorbent.

FIG. 9 is a side view of the urinary incontinence device depicted in FIG. 8 when in an expanded state after absorbing fluid showing the outward bulge cause by the expansion of the first and second absorbents.

FIG. 10 is a top view of still another embodiment of the urinary incontinence device showing the second absorbent having a length that is less than 75% of the length of the first absorbent and a width that is less than 75% of the width of the first absorbent.

FIG. 11 is a side view of the urinary incontinence device depicted in FIG. 10 when in an expanded state after absorbing fluid showing the outward bulge caused by the expansion of the first and second absorbents.

FIG. 17 is a flow diagram of a method for alleviating female urinary incontinence.

FIG. 18 is a flow diagram of a method for alleviating female urinary incontinence including removing the device from a woman's vagina.

DETAILED DESCRIPTION OF THE PREFERRED EMBODIMENTS

Figure 1:
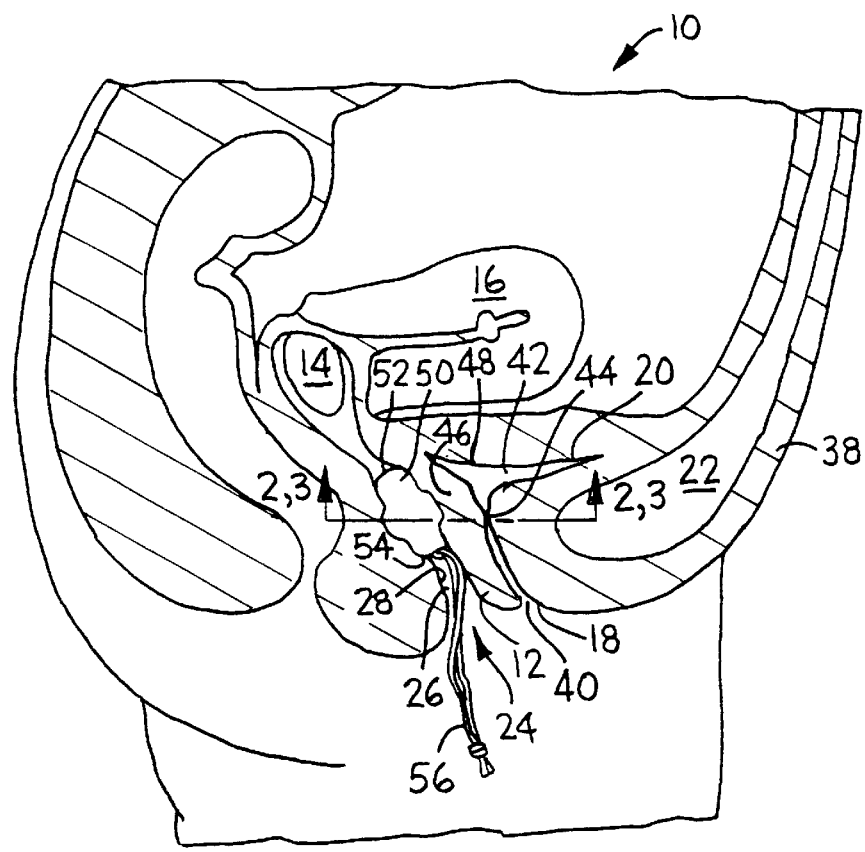
FIG. 1 is a mid-sagittal section of a human torso showing a urinary incontinence device positioned in the vaginal canal and cooperating with the symphysis pubis to allow the urethral tube to be compressed upon itself and alleviate urinary incontinence during episodes of increased intra-abdominal pressure.
Figure 2:
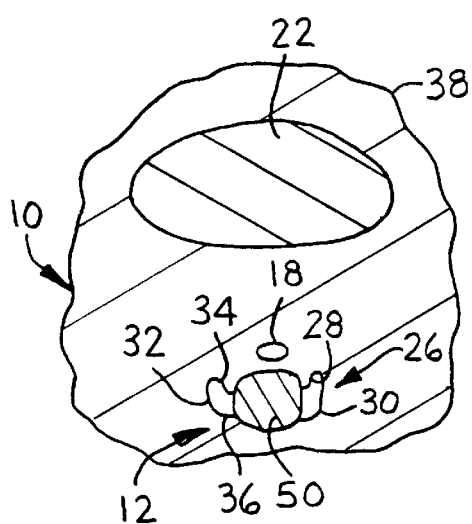
FIG. 2 is a sectional view taken along line 2—2 of FIG. 1 when the urinary incontinence device is in a non-expanded condition and the cross-section of the vaginal canal and the urethra are in a relaxed configuration.

Referring to FIGS. 1 and 2, a human torso 10 of a female is depicted showing the vagina 12, a cervix 14, a uterus 16, a urethra 18, a bladder 20 and a symphysis pubis 22. The vagina 12 has an introital opening 24 which exits the human body 10 and contains a vaginal canal 26 which extends from the introital opening 24 to the cervix 14. The vaginal canal 26 has a length which ranges from between about 4 inches to about 6 inches (about 102 millimeters (mm) to about 153 mm) in most woman. The cervix 14 is the entrance to the womb and is located between the upper aspect of the vaginal canal 26 and the uterus 16. The vaginal canal 26 has an inner periphery 28. The inner periphery 28 is made up of right and left lateral walls, 30 and 32 respectively, an anterior wall 34 and a posterior wall 36, see FIG. 2. The four walls 30, 32, 34 and 36 encompass the entire 360 degrees of the inner periphery 28. The anterior wall 34 is located closest to the urethra 18 and the urethra 18 is located between the symphysis pubis 22 and the vagina 12. The vaginal canal 26 can be divided into three approximately equal sections, each representing a third of the overall length. Each section is approximately 2 inches (approximately 51 mm) in length. The middle third of the vaginal canal 26 is the most important section for alleviating female urinary incontinence because of its proximity to the external sphincter 44 of the urethra 18 and is the location where a urinary incontinence device should be positioned. The middle third of the vaginal canal 26 also is horizontally offset from the symphysis pubis 22, which is a bony prominence situated adjacent to a front portion 38 of the human torso 10. Cooperation between a urinary incontinence device positioned in the middle third of the vagina 12 and the symphysis pubis 22 allows the urethra 18 to be compressed upon itself thereby alleviating or significantly reducing involuntary urine flow from the bladder 20.

The urethra 18, also referred to as a urethral tube, is a hollow tube which extends from a first external opening 40, which exits the human body 10, to a second internal opening 42 situated at the lower surface of the bladder 20. The urethral tube 18 has a length of about 1.5 inches (about 38 mm) in most women. The urethral tube 18 functions to discharge urine, which is temporarily stored in the bladder 20, from the human body. The urethral tube 18 has an external sphincter muscle 44 located along a portion of its length. The external sphincter muscle 44 is situated below the second opening 42 and is a ringlike structure that normally allows for of the urethral tube 18 to prevent the involuntary passage of urine therethrough. The relaxation of the external sphincter muscle 44 by normal physiological functioning contributes to urine being voluntarily expelled from the human body.

Still referring to FIG. 1, the human torso 10 further includes musculature and body tissue located in the urethrovaginal myofascial area 46 which is situated between the vagina 12 and the symphysis pubis 22. The bladder 20 lies posterior and superior to the symphysis pubis 22 and is separated from the rectum by the vagina 12 and in part by the uterus 16. The ureters (not shown), which transport urine from the kidneys to the bladder 20, pass from the pelvis to the posterior aspect of the urinary bladder 20. The fundus vesicae 48, into which both ureters terminate, is located adjacent to the anterior wall 34 of the vagina 12.

Figure 3:
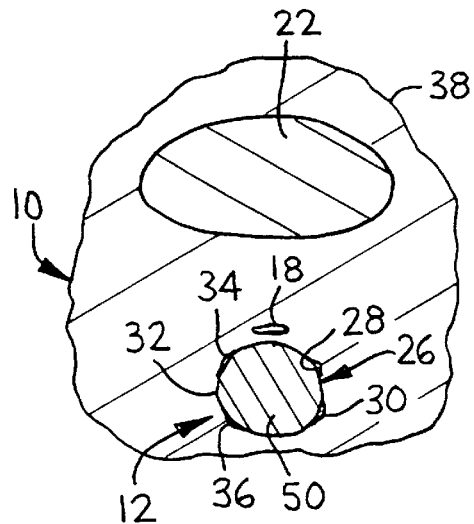
FIG. 3 is a sectional view taken along line 3—3 of FIG. 1 showing the urinary incontinence device in an expanded condition closing off the cross-section of the vaginal canal and providing a supportive backdrop for closing off the urethra.

Referring to FIGS. 1–3, a urinary incontinence device 50 is shown positioned in the middle third of the length of the vaginal canal 26. The urinary incontinence device 50 is depicted in an expanded state after having absorbed some amount of body fluid. The urinary incontinence device 50, before absorbing body fluid is a generally cylindrical member having an insertion end 52 and a trailing end 54. A withdrawal means 56, preferably in the form of an elongated string or ribbon is securely attached to the urinary incontinence device 50 and facilitates the removal of the urinary incontinence device 50 from the vaginal canal 26. When the user is ready to remove the urinary incontinence device 50, she will pull downward on the withdrawal string 56. This action will cause the urinary incontinence device 50 to be comfortably withdrawn from the vaginal canal 26.

The withdrawal string 56 can be constructed from various types of threads or ribbons. A thread or ribbon made from 100 percent cotton fibers works well. The withdrawal string 56 should have a length which extends beyond the trailing end 54 from between about 2 inches (about 51 mm) to about 8 inches (about 203 mm). Preferably, the withdrawal string 56 should have a length which extends beyond the trailing end 54 from between about 4 inches (about 102 mm) to about 6 inches (about 152 mm), and most preferably, by about 5 inches (about 127 mm). The withdrawal string 56 can be dyed and/or treated with an anti-wicking agent, such as wax, before being secured to the urinary incontinence device 50. The anti-wicking agent will reduce and prevent internal body fluid from wicking along the withdrawal string 56 and contacting the inner surface of a woman's undergarment. A dry, clean withdrawal string 56 is preferred by the user, especially when she goes to remove the urinary incontinence device 50 from her vagina 12.

Referring to FIGS. 1 and 2, the urinary incontinence device 50 is shown positioned in the middle third of the length of the vaginal canal 26. The urinary incontinence device 50 is designed to bridge across the vagina 12 and support the musculature and body tissue located in the urethro-vaginal myofascial area 46. In FIG. 2, the urinary incontinence device 50 is shown in a non-expanded state with the insertion end 52 aligned adjacent to a woman's external sphincter muscle 44. The urinary incontinence device 50 is shown in direct contact with the anterior wall 34 and the posterior wall 36 while being spaced apart from the right and left lateral walls, 30 and 32 respectively. The urinary incontinence device 50 cooperates with the symphysis pubis 22 to compress the urethral tube 18 therebetween.

Referring to FIG. 3, the urinary incontinence device 50 is shown in an expanded state having absorbed moisture and body fluid. In the expanded state, the urinary incontinence device 50 has an overall larger cross-sectional area. In addition, a portion of the length of the urinary incontinence device 50 will expand farther radially outward than the remaining portions of the urinary incontinence device 50 and will contact the entire inner periphery of the vaginal canal 26. In other words, a portion of the urinary incontinence device 50 is directly touching all four interior walls 30, 32, 34 and 36 of the vaginal canal 26 and is providing a supportive backdrop for the urethral tube 18. The urethral tube 18 can now be compressed sufficiently to intercept the involuntary flow of urine and additionally provides support to the external sphincter muscle 44 so that it can function properly. By permitting the urethral tube 18 to be compressed upon itself between the urinary incontinence device 50 and the symphysis pubis 22, one can limit the involuntary flow of urine from the bladder 20.

Referring to FIG. 4, the urinary incontinence device 50 includes a first absorbent 58 having a first surface 60, a second surface 62, a length "$L_1$," and a width "$W_1$". The first absorbent 58 is preferably an elongated member having a uniform in thickness and a rectangular shape. A non-uniform thickness as well as other configurations can be utilized if desired. The first absorbent 58 can be formed from absorbent fibers that are assembled into an absorbent sheet or ribbon. The first absorbent 58 can include cellulose fibers, such as cotton and/or rayon. The first absorbent 58 can be 100 percent (%) cotton, 100% rayon or a blend of cotton and rayon fibers. Examples of some blends which work well include a blend of about 15% cotton and about 85% rayon; a blend of about 70% cotton and about 30% rayon; a blend of about 60% cotton and about 40% rayon; a blend of about 25% cotton and about 75% rayon; and a blend of about 6% cotton and about 94% rayon. The particular blend of fibers can vary depending upon one's preference.

When cotton fibers are used, the cotton fibers should have a staple length of from between about 5 mm to about 20 mm. The cotton fibers should generally have a fiber size of from between about 150 microns to about 280 microns. The cotton fibers can also be bleached if desired. Bleaching will make the cotton fibers whiter in appearance.

When rayon fibers are present, the rayon fibers should have a staple length of from between about 20 mm to about 35 mm. The rayon fibers should have a denier of from between about 2 to about 6. Denier is a unit of fineness of yarn based on a standard of 50 milligrams (mg) for 450 meters of yarn. The rayon fibers can have various cross-sectional configurations including a circular elongated, a bi-lobal cross-sectional configuration, or a tri-lobal cross-sectional configuration. Other cross-sectional configurations can also be used. The bi-lobal configuration has a cross-sectional profile, which looks like a dog bone, while the tri-lobal configuration has a cross-sectional profile, which looks like a "Y". The rayon fibers can also be bleached if desired.

The first absorbent 58, when formed from an absorbent sheet or ribbon can be constructed using at least two processes known to those skilled in the art. Two of such processes are known as "carding" and "airlaying." Depending upon the desired absorbency one desires in the finished urinary incontinence device 50, the basis weight of the first absorbent 58 can vary. It should also be mentioned that the first absorbent 58 could contain a ratio of absorbent fibers to non-absorbent fibers to reduce cost, increase performance, facilitate the expandability of the second absorbent 64, etc. The first absorbent 58 can contain from between about 1 to about 100% absorbent fibers or any percentage therebetween.

The length $L_1$, of the first absorbent 58 can vary from between about 3 inches (about 76 mm) to about 8 inches (about 203 mm). The width $W_1$ of the first absorbent 58 can vary from between about 1.75 inches (about 44 mm) to about 3 inches (about 76 mm). Preferably, the length $L_1$ of the first absorbent 58 is less than about 7 inches (about 178 mm) and the width $W_1$ of the first absorbent 58 is less than about 2.5 inches (about 64 mm). Most preferably, the length $L_1$ of the first absorbent 58 is about 6 inches (about 152 mm) and the width $W_1$. of the first absorbent 58 is about 2.25 inches (about 57 mm).

The first absorbent 58 also has a longitudinal axis x—x, a transverse axis y—y and a vertical axis z—z. The first and second surfaces 60 and 62 of the first absorbent 58 are aligned opposite to one another. As depicted in FIG. 4, the first surface 60 will eventually become the interior surface and the second surface 62 will become the exterior surface.

Still referring to FIG. 4, the urinary incontinence device 50 further includes a second absorbent 64 that is positioned adjacent to the first surface 60 of the first absorbent 58. By "adjacent to" it is meant that the second absorbent 64 can be in direct face to face contact with the first absorbent 58. Alternatively, the second absorbent 64 can be spaced apart from the first absorbent 58 by one or more layers. For example, one or more layers of an absorbent tissue can be positioned between the first and second absorbents, 58 and 64 respectively. Likewise, one or more layers of a surge material or a wicking material could be positioned between the first and second absorbents, 58 and 64 respectively. The only restriction is that any intervening layer or layers positioned between the first and second absorbents, 58 and 64, should not unduly restrict the expansion of the first and/or second absorbents, 58 and 64 respectively. Preferably, the second absorbent 64 is in direct contact with the first surface 60 of the first absorbent 58.

The second absorbent 64 can be constructed of the same material or from a different material than was used to construct the first absorbent 58. The second absorbent 64 has a length "$L_2$" and a width "$W_2$" and is aligned along the longitudinal axis x—x. The second absorbent 64 can be offset from the longitudinal axis x—x if desired. The second absorbent 64 is shown having a rectangular shape, although other configurations can be utilized if desired. The length $L_2$ of the second absorbent 64 can be equal to, less than or be greater than the length $L_1$ of the first absorbent 58. Preferably, the first and second absorbents, 58 and 64 respectively, have the same length. The width $W_2$ of the second absorbent 64 is less than about 75 percent (%) of the width $W_1$ of the first absorbent 58. Preferably, the width $W_2$ of the second absorbent 64 is less than about 50% of the width $W_1$ of the first absorbent 58, and most preferably, the width $W_2$ of the second absorbent 64 is less than about 35% of the width $W_1$ of the first absorbent 58. The width $W_2$ of the second absorbent 64 can range from between about 2.25 inches (about 57 mm) to about 1 inch (about 25 mm).

Like the first absorbent 58, the basis weight of the second absorbent 64 can vary. Likewise, the configuration of the second absorbent 64 can vary in thickness along its length and/or width. The U.S. Food and Drug Administration (FDA) has set absorbency standards for tampons. The urinary incontinence device 50 can be constructed to coincide with the normal sizes of tampons, namely: "junior", "regular", "super" and "super-plus". In order to coincide with the FDA standards for these four sizes, the first and second absorbents, 58 and 64 respectively, can be targeted to have a combined basis weight of about 100 grams per square meter (gsm), 120 gsm, 170 gsm and 230 gsm, respectively. Typically, the carding process is controlled to produce the first absorbent 58 with a width $W_1$ of from between about 40 mm to about 60 mm, preferably, about 50 mm. The basis weight and/or the length of the first and second absorbents, 58 and 64 respectively, can also be adjusted to form the different size urinary incontinence devices 50.

It should be noted that the absorbent capacity of the second absorbent 64 could be less than, equal to or greater than the absorbent capacity of said first absorbent 58, when measured in grams/grams. Preferably, the absorbent capacity of the first and second absorbents, 58 and 64 respectively, will be approximately equal.

Still referring to FIG. 4, the urinary incontinence device 50 can include a cover 66 that partially or fully encloses the first and second absorbents, 58 and 64 respectively. The cover 66 is an optional element and need not be present to form the urinary incontinence device 50. However, the cover 66 can provide a smooth outer surface that may or may not be chemically treated to facilitate insertion and removal into and out of a woman's vagina. When present, the cover 66 should be extensible or stretchable so as to accommodate the outward or radial expansion of the first and second absorbents, 58 and 64 respectively, as they absorb body fluid. The cover 66 could have a length that is less than, equal to or greater than the length of the first absorbent 58. The cover 66 could have a width that is less than, equal to or greater than the width of the first absorbent 58. When the width of the cover 66 is equal to or less than the width $W_1$ of the first absorbent 58, the insertion and trailing ends, 52 and 54 respectively, can be exposed. When the cover 66 has a greater width dimension than the first absorbent 58, the cover 66 could be folded over upon itself at each end to completely enclose the first and second absorbents, 58 and 64. The cover 66 can be bonded to itself by heat, pressure, a combination of heat and pressure, or by some other conventional means known to those skilled in the art. If the cover 66 is formed from a material which does not readily bond to itself, an adhesive, glue or other bio-compatible bonding or fastening medium can be used. If desired, the cover 66 may be simply folded over upon itself.

The cover 66 is preferably liquid-permeable. By "liquid-permeable" it is meant that body fluid is able to pass through the cover 66 in a quick and efficient manner. The cover 66 can be hydrophilic, hydrophobic or a combination of each. By "hydrophilic" it is meant that the cover 66 has an affinity for absorbing or tending to combine with water. By "hydrophobic" it is meant that the cover 66 is antagonistic to or tends not to allow the passage of body fluid. The cover 66 can also be treated with a surfactant or some other chemical to make it hydrophilic, hydrophobic or to make it more hydrophilic or more hydrophobic. Surfactants having high lubricity and hydrophobicity and which are non-irritating to the vaginal mucosa are preferred since they discourage the attraction, accumulation and retention of any resident vaginal fluid. Preferably, the area of the cover 66 that is aligned with the second absorbent 64 is hydrophilic so that body fluid will be attracted to this area.

The cover 66 can be formed from a woven or nonwoven materials having a porous substrate. Woven materials include textile fabrics that can be made from rayon, cotton, or polyolefins. The polyolefins can be either staple or continuous filaments. The nonwoven materials can include spunbond, bonded-carded webs and hydroentangled webs. One material that works well as a cover is a 0.4 ounces per square yard (osy) spunbond polypropylene having a crepe of at least 30%. Another material that works well as a cover is a 0.6 osy spunbond polypropylene having a crepe of at least 30%. Spunbond and bonded-carded webs are commercially available from Kimberly-Clark Corporation having an office at 401 N. Lake Street, Neenah, Wis. 54956.

The cover 66 can further be formed from an apertured thermoplastic film having either a two or three-dimensional thickness. Apertured thermoplastic films are available from several commercial vendors. One such vendor is Pantex srl, Pantex Sud sri, Via Terracini snc, having an office at 51031 Agliana, Pistoia, Italy. A second vendor is Applied Extrusion Technology having a mailing address of P.O. Box 582, Middleton, Del. 19709.

The cover 66 can also be treated with an aqueous solution to reduce frictional drag, to give the urinary incontinence device 50 a permanent wettability and/or to enhance the ease of insertion into and removal from a woman's vagina. The thickness of the cover 66 can range from between about 0.1 mm to about 5 mm. Preferably, the thickness of the cover 66 is less than about 0.5 mm, and most preferably, less than about 0.2 mm.

It should be noted that in FIG. 4, the cover 66 is shown positioned adjacent to the first absorbent 58. However, the cover 66 could be positioned adjacent to the second absorbent 64 if desired.

In FIG. 4, one means of securing the withdrawal string 56 to the first urinary incontinent device 50 is depicted. An aperture or opening 68 is formed through the first absorbent 58 and the cover 66 and the withdrawal string 66 is passed through the aperture 68. The aperture 68 can be formed parallel to the vertical axis z—z or at an angle thereto. Preferably, the aperture 68 is spaced a short distance from the trailing end 54. The aperture 68 can be located a distance of from between about 0.1 inches (about 2.5 mm) to about 0.5 inches (about 12.7 mm) from the trailing end 54. Although the aperture 68 can be located almost anywhere in the first absorbent 58, it preferably is located about 0.25 inches (about 6.4 mm) from the trailing end 64.

It should be noted that other ways of attaching the withdrawal string 56 to the urinary incontinence device 50 can be used and are known to those skilled in the art.

The withdrawal string 56 can pass through the aperture 68 and be looped upon itself so as to be cinched and permanently secured to the urinary incontinence device 50. The aperture 68 can be formed with a needle, an awl or some other type of piercing device known to those skilled in the art. The free ends of the withdrawal string 56 are then tied in a knot 70 to assure that the withdrawal string 56 will not separate from the urinary incontinence device 50. The knot 70 also serves to prevent fraying of the withdrawal string 56 and to provide a place or point where a woman can grasp the withdrawal string 56 when she is ready to remove the urinary incontinence device 50 from her vagina 12. It should also be noted that the aperture 68 could also be formed through the second absorbent 64 and/or the cover 66 if desired.

Referring now to FIGS. 5 and 6, the first and second absorbents, 58 and 64 respectively, and the cover 66 are depicted as being radially wound along the longitudinal axis x—x to form a softwind 72. Another way of stating this to say that the first and second absorbent, 58 and 64 respectively, and the cover 66 when present, are rolled up parallel to the transverse axis y—y to form a softwind 72. It is also possible to fold the first and second absorbents, 58 and 64 respectively, perpendicularly to the longitudinal axis x—x to form a softwind. After the softwind 72 is formed, it is radially compressed into an elongated pledget 74. The pledget 74 is the finished version of the urinary incontinence device 50. The compressed pledget 74 can have any desired shape but preferably it will have a cylindrical shape with a round or circular cross-sectional configuration. Most preferably, the pledget 74 will have a uniform cross-sectional area before insertion into a woman's vagina 12. The diameter of the pledget 74 can range from between about 5 to about 64 mm. Alternatively, the pledget 74 could have a rectangular cross-sectional configuration. The elongated pledget 74 has a length $L_3$ and a width $W_3$. When the pledget 74 is round in cross-section area, its diameter will be equal to its width $W_3$. The length $L_3$ of the pledget 74 can range from about 0.4 inches (about 10 mm) to about 4.7 inches (about 120 mm). Preferably, the length $L_3$ of the pledget 74 can range from between about 1.5 inches (about 38 mm) to about 2.5 inches (about 65 mm), and most preferably, the length $L_3$ of the pledget 74 is at least about 2 inches (about 51 mm). The width $W_3$ of the pledget 74 can range from between about 0.2 inches (about 5 mm) to about 2.5 inches (about 65 mm). Preferably, the width $W_3$ of the pledget 74 can range from between about 0.5 inches (about 12.7 mm) to about 2 inches (about 51 mm), and most preferably, the width $W_3$ of the pledget 74 is less than about 1.6 inches (about 40 mm).

Referring again to FIG. 1, the insertion end 52 of the pledget 74 is designed to be the first part of the pledget 74 to enter a woman's vagina 12. When properly inserted into the vagina 12, the entire pledget 74 will be positioned in the upper two thirds of the length of the vaginal canal 26. Preferably, the urinary incontinence device 50 occupies the middle 2 inches (about 51 mm) of the vaginal canal 26. The urinary incontinence device 50 provides a supportive backdrop for the body tissue and muscles located in the urethro-vaginal myofascial area 46. In this position, and knowing the urethra 18 and the vagina 12 are closely approximated, the urinary incontinence device 50 will be aligned with the upper portion of the urethral tube 18 and will provide a supportive backdrop for at least half of the urethral tube 18. During episodes of increased intra-abdominal pressure, the compression that occurs to the urethro-vaginal myofascial area 46, between the symphysis pubis 22 and the urinary incontinence device 50, the urethral tube 18 to be compressed upon itself. This action will apply pressure against the external sphincter muscle 44 and allow it to acquire a more normal configuration. These two functions assist one another in alleviating involuntary urine flow from the bladder 20.

The pledget 74 is capable of expanding radially outward as well as lengthwise. It is the expansion of a portion of the pledget 74 in the radial or width direction that is important. The pledget 74 can be designed to expand to approximately twice its width $W_3$. For example, a pledget 74 having a width $W_3$ of about 0.2 inches (about 5 mm) could expand to about 0.4 inches (about 10 mm). Likewise, a pledget 74 having a width $W_3$ of about 2.5 inches (about 65 mm) could expand to about 5.0 inches (about 120 mm). As the first absorbent 58 and primarily the second absorbent 64 expand, the pledget 74 will increase its cross-sectional area. The portion of the pledget 74 that contains the second absorbent 64 will bulge outward beyond the expanded portion that contains only the first absorbent 58 and this bulging section will exert a pressure against the inner periphery 28 of the vaginal canal 26. This pressure can range from between about 0.15 pounds per square inch (psi) to about 2.5 psi depending on the anatomy of the user. This pressure will be directed against the full 360 degrees of the inner periphery 28 over a distance corresponding to the width $W_2$ of the second absorbent 64.

It should be noted that when the urinary incontinence device 50 is properly positioned in the vagina 12, only the withdrawal string 56 would be exposed.

Referring to FIG. 7, a side view of the urinary incontinence device 50 is shown after it has expanded by absorbing body fluids while being positioned within the vaginal canal 26. One will notice that the entire cross-sectional area of the urinary incontinence device 50 has expanded from a diameter or width $W_3$ to a larger diameter or width denoted by the dimension "$t_1$". This expansion of the pledget 74 occurs over its entire length from the insertion end 52 to the trailing end 54. The cross-sectional area of the pledget 74 expands to the larger dimension "$t_2$" due to the swelling of the first absorbent 58 as it absorbs body fluid. In addition, a bulge, herniation or rounded protuberance 76 is formed by the outward expansion of the first and second absorbents, 58 and 64 respectively. This bulge or outward swelling 76 will occur over the width $W_2$ of the second absorbent 64 and will extend farther outward to a dimension "$t_2$". The dimension "$t_2$" can range from between about 1 mm to about 20 mm depending on the initial diameter or width $W_3$ of the pledget 74. The difference in dimension between $t_2$ and $t_1$ should be at least 10%. This means that the cross-sectional area of the pledget 74 has expanded at least 10% more over the distance represented by $W_2$ than over the remaining portions of the pledget 74. Preferably, the difference between $t_2$ and $t_1$ ranges from between about 10% to about 50%. Most preferably, the difference between $t_2$ and $t_1$ ranges from between about 15% to about 40%. This bulge 76 will bring the portion of the urinary incontinence device 50 represented by $W_2$ into intimate contact with all four walls 30, 32, 34 and 36 of the vaginal canal 26. In doing so, the bulge 76 will occupy the entire cross-sectional area of the vagina 12 for a distance $W_2$ of from between about 2.25 inches (about 57 mm) to about 0.25 inches (about 6 mm). Preferably, the distance $W_2$ will range from between about 2 inches (about 51 mm) to about 0.5 inches (about 12.7 mm). Most preferably, the distance $W_2$ will be less than about 1.5 inches (about 38 mm).

The bulge or outward swelling 76 will occupy a section of the vaginal canal corresponding to the surface area $W_2$. The bulge 76 will provide support for the external sphincter muscle 44 so that it can close off the urethral tube 18 and prevent urine in the bladder 20 from passing through to the external opening 40. Furthermore, the relative position and proximity of the bulge 76 within the vagina 12 will enable the urethral tube 18 to be compressed upon itself and provide a supportive backdrop in cooperation with the symphysis pubis 22.

Referring to FIGS. 8 and 9, an alternative embodiment of a urinary incontinent device 50' is depicted. In this embodiment, the second absorbent 64' has a length $L_4$ that is less than 50% of the length $L_1$ of the first absorbent 58. This length $L_4$ starts to the right of the transverse axis y—y and terminates at point B. In addition, the second absorbent 64' has a width $W_4$ that is less than about 35% of the width $W_1$ of the first absorbent 58. Furthermore, as the second absorbent 64' is radially wound along the longitudinal axis x—x, starting at point A, the second absorbent 64' will be located in the outer perimeter of the finished softwind. This means that after the softwind is compressed into an elongated pledget 74', the second absorbent 64' will be absent from center of the pledget 64' and instead be located adjacent to the outer periphery of the pledget 74'. This will enable a smaller quantity of the second absorbent material 64' to be used while still providing for adequate outward swelling upon contact with body fluid. This construction will enable the first and second absorbent 58 and 64' to swell outward upon contact with body fluid and create a bulge 76'. The bulge 76' will extend over a distance equal to the dimension of the width $W_4$. As stated earlier, the bulge 76' should extent outward beyond the expanded remaining portions of the pledget 74' by at least 10%. The profile of the bulge 76' can vary and is shown to have a narrower ringlike shape than the bulge 76 depicted in FIG. 7.

Referring to FIGS. 10 and 11, still another embodiment of a urinary incontinent device 50" is depicted. In this embodiment, the second absorbent 64" has a length $L_5$ that is less than 75% of the length $L_1$ of the first absorbent 58. The second absorbent 64" is centered on the first absorbent 58 along the longitudinal axis x—x and is spaced an equal distance away from points A and B. In addition, the second absorbent 64" has a width $W_5$ that is less than about 75% of the width $W_1$ of the first absorbent 58. Furthermore, as the second absorbent 64" is radially wound along the longitudinal axis x—x, starting at point A, the second absorbent 64' will be located in the center of the finished softwind. This means that after the softwind is compressed into an elongated pledget 74" the second absorbent 64" will be located midway between the axis y—y and the outer periphery of the pledget 74". This construction will enable the first and second absorbent 58 and 64" to swell outward upon contact with body fluid and create a bulge 76". The bulge 76" will extend over a distance equal to the dimension of the width $W_5$.

Based upon the three embodiments depicted above, it should be evident to one skilled in the art that the urinary incontinent device 50, 50' and 50" can be constructed to create a unique, predetermined cross-sectional configuration once it swells following contact with body fluids. If one desires a wider ring of protection, one can simply make the second absorbent 64 wider. Likewise, if a narrow ring is desired, a second absorbent 64 can be utilized which has a relatively narrow width. If one desires a less protruding bulge, then one can reduce the amount of material used to form the second absorbent 64, 64' or 64" or reduce the length of the second absorbent 64, 64' or 64".

Figure 12:
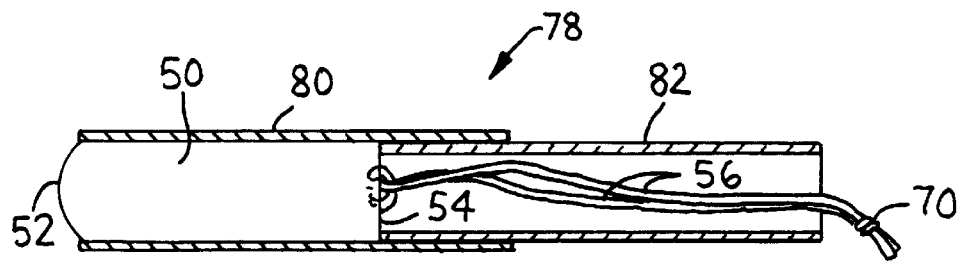
FIG. 12 is a side view of a urinary incontinence device housed in an applicator.

Referring to FIG. 12, the urinary incontinence device 50 is shown retained or housed in an applicator 78. The applicator 78 will facilitate insertion of the urinary incontinence device 50 into a woman's vagina 12. The applicator 78 can be identical to a tampon applicator, if desired. The applicator 78 is depicted as a two-piece telescoping applicator having a hollow outer tube 80 and a hollow inner tube 82. The urinary incontinence device 50 is positioned within the outer tube 80 such that the inner tube 82, which has a smaller diameter, can be pushed against the trailing end 54. This action will cause the urinary incontinence device 50 to be expelled from the outer tube 80. The applicator 78 can be constructed of paper, cardboard or plastic. One example of an applicator is taught in U.S. Pat. No. 5,795,346 which issued to Achter et al. on Aug. 18, 1998 and is entitled: "TAMPON HAVING A RESILIENT MEMBER".

It should be recognized that the urinary incontinence device 50 could be digitally inserted into a woman's vagina 12. For digital insertion, a woman would use one of her fingers to push on the trailing end 54 of the urinary incontinence device 50, 50' or 50" so that the insertion end 52 could easily enter her vagina. With digital insertion, there would be no need for an applicator.

Figure 13:
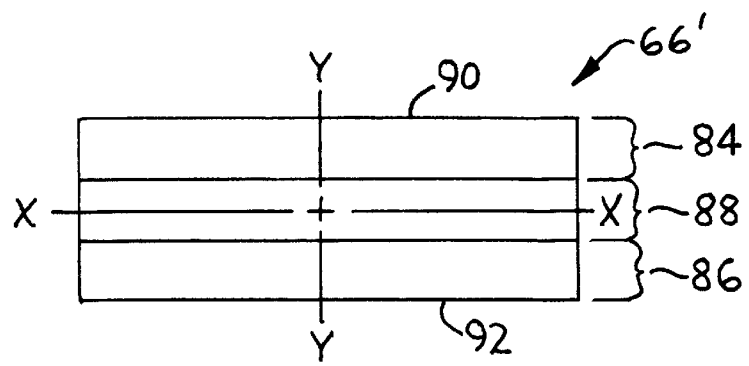
FIG. 13 is a top view of a cover having three longitudinally extending zones with the first and second zones being treated with a surfactant to render them hydrophobic and the third or central zone being hydrophilic.

Referring FIG. 13, an alternative embodiment of a cover 66' is depicted. The cover 66' is an elongated member having a first zone 84, a second zone 86 and a third or central zone 88. The first zone 84 is located adjacent to a first edge 90 and the second zone 86 is located adjacent to a second edge 92. The first and second edges 90 and 92 will be aligned close to the insertion end 52 and the trailing end 54, respectively, once the cover 66' and the first and second absorbents (not shown) are formed into a softwind. The first and second zones 84 and 86 of the cover 66' can be treated with a surfactant to render these two zones hydrophobic. The third or central zone 88 of the cover 66' is located between the first and second zones 84 and 86 and is treated to be hydrophilic. This means that the third or central zone 88 has a greater affinity for water than the first and second zones, 84 and 86 respectively. Because of this, the central or third zone 88 will be able to absorb body fluid quicker than the first and/or second zones, 84 and 86 respectively, and hence will likely bulge or swell outward to a greater extent.

It should be noted that the third or central zone 88 of the cover 66' can have a width that is less than, equal to or greater than the width of either the first and/or second zones, 84 and 86 respectively. Preferably, the width of the third or central zone 88 will be approximately equal to the width of the first zone 84 which in turn is equal to the width of the second zone 86. Another way of stating this is to say that all three zones 84, 86 and 88 have the same width. It is also preferable to size the width of the third zone 88 to be approximately equal to the width $W_2$, $W_4$ or $W_5$ of the second absorbent 64, 64' or 64". This will facilitate swelling of the first absorbent 58 and the second absorbent 64, 64' or 64" to form the bulge 76, 76' or 76".

Figure 14:
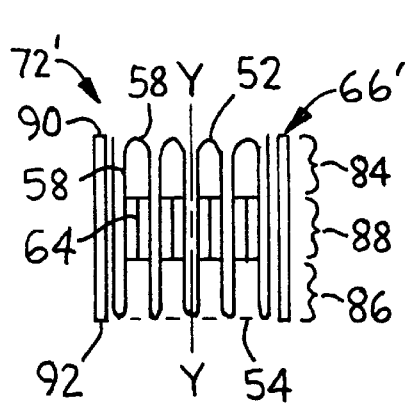
FIG. 14 is a vertical cross-sectional view of the first and second absorbents being folded and enclosed by the cover depicted in FIG. 13 to form a softwind.
Figure 15:
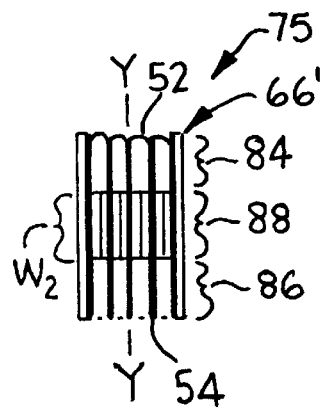
FIG. 15 is a vertical cross-sectional view of the softwind depicted in FIG. 14 after it has been radially compressed to form an elongated pledget.
Figure 16:
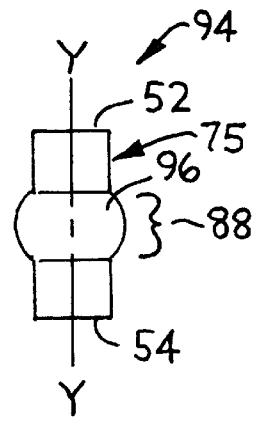
FIG. 16 is a vertical cross-sectional view of the pledget depicted in FIG. 15 after it has absorbed fluid and the first and second absorbents have expanded to create an outward bulge.

Referring to FIGS. 14–16, one will notice that the first and second absorbents, 58 and 64 respectively, are folded over one another multiple times instead of being radially wound. This folding action produces a softwind 72', see FIG. 14. The softwind 72' is then radially compressed into an elongated pledget 75, see FIG. 15. The second absorbent 64 is located in the central portion of the pledget 75 and has a width $W_2$ that corresponds to the linear dimension of the hydrophilic third zone 88. This folding of the first and second absorbents, 58 and 64 respectively, produces a urinary incontinent device 94, see FIG. 16. The hydrophilic third zone 88 of the cover 66' allows the first and second absorbents, 58 and 64 respectively, to quickly absorb body fluid and swell outward and form a bulge 96. The size and shape of the bulge 96 can be dictated by the absorbent capacity of the first and second absorbents, 58 and 64 respectively, as well as by the amount of absorbent material present and the way the first and second absorbents, 58 and 64 respectively, are folded. The extent to which the softwind 75 is compressed can also influence the size and shape of the bulge 96.

METHOD

The method of alleviating female urinary incontinence, especially during episodes of increased intra-abdominal pressure will now be explained with reference to the flow diagrams shown in FIGS. 17 and 18. The method for alleviating female urinary incontinence includes the steps of providing a urinary incontinence device 50, 50', 50" or 94 having a first absorbent 58 and a second absorbent 64, 64' or 64". The first absorbent 58 has a length $L_1$, a width $W_1$ and a longitudinal axis x—x. The second absorbent 64, 64' or 64" is positioned adjacent to the first absorbent 58 and is aligned along the longitudinal axis x—x. The second absorbent 64, 64' or 64" has a width $W_2$, $W_4$ or $W_5$ that is less than about 80% of the width $W_1$ of the first absorbent 58. Preferably, the second absorbent 64, 64' or 64" has a width $W_2$, $W_4$ or $W_5$ that is less than about 50% of the width $W_1$ of the first absorbent 58. Most preferably, the second absorbent 64, 64' or 64" has a width $W_2$, $W_4$ or $W_5$ that is less than about 35% of the width $W_1$ of the first absorbent 58. The first absorbent 58 and the second absorbent 64, 64' or 64" are formed into a softwind 72 or 72' that is compressed into an elongated pledget 74, 74', 74" or 75 having a cross-sectional area. Preferably, the cross-sectional area of the pledget 74, 74', 74" or 75 is uniform over its entire length. The pledget 74, 74', 74" or 75 has an insertion end 52 and a trailing end 54. The first absorbent 58 and the second absorbent 64, 64' or 64" are capable of absorbing fluid and expanding the cross-sectional area of the pledget 74, 74', 74" or 75 to a larger dimension, denoted "$t_1$" in FIG. 7. The second absorbent 64, 64' or 64" causes a portion of the cross-sectional area of the pledget 74, 74', 74" or 75 to expand farther outward to provide a supportive backdrop for a woman's urethra 18 when inserted into a woman's vagina 12.

The method also includes inserting the urinary incontinence device 50, 50', 50" or 94 into a woman's vagina 12 with the insertion end 52 entering first. The vagina 12 has a vaginal canal 26 with an inner periphery 28 made up of right and left lateral walls, 30 and 32 respectively, an anterior wall 34 and a posterior wall 36. The urinary incontinence device 50, 50', 50" or 94 will contact at least two of the walls 30, 32, 34 and 36 upon initial placement in the vagina 12. The urinary incontinence device 50, 50', 50" or 94 is then positioned in the upper two thirds of the length of the vaginal canal 26 with the insertion end 52 nearly aligned adjacent to a woman's external sphincter muscle 44. The external sphincter muscle 44 is a part of a woman's urethral tube 18. The urinary incontinence device 50, 50', 50" or 94 cooperates with a woman's symphysis pubis 22 to compress the urethral tube 18 therebetween when intra-abdominal pressure increases.

The entire urinary incontinence device 50, 50', 50" or 94 is then allowed to expand within the vaginal canal 26 such that a portion of the urinary incontinence device 50, 50', 50" or 94 that corresponds to the location of the second absorbent 64, 64' or 64" increases in cross-sectional area to a greater extent than the remaining portions of the urinary incontinence device 50, 50', 50" or 94. This means that the portion of the pledget 74, 74', 74" or 75 that contains the first absorbent 58 and the second absorbent 64, 64' or 64" expands outward in the radial direction to a greater extent than the portions of the pledget 64, 64' or 64" that are made up of only the first absorbent 58. The presence of the cover 66 is not important for the cover 66 does not expand to any appreciable extent. The cover 66 should however, be extensible or stretchable enough so that it can easily accommodate the bulging area occupied by the first absorbent 58 and the second absorbent 64, 64' or 64". The expanded cross-sectional area of the first absorbent 58 and the second absorbent 64, 64' or 64" will form an outwardly extending bulge 76, 76', 76" or 96 that can have a ringlike appearance. This ringlike bulge 76, 76', 76" or 96 most intimately contacts all four interior walls 30, 32, 34 and 36 of said vaginal canal 26 at the area of the bulge $W_2$, $W_4$, or $W_5$ and provides a supportive backdrop for the urethral tube 18.

The method further includes permitting the urethral tube 18 to be compressed upon itself between the urinary incontinence device 50, 50', 50" or 94 and the symphysis pubis 22 thereby limiting involuntary urine flow. The urethra or urethral tube 18 has a length of about 1.5 inches (about 37 mm) and the urinary incontinence device 50, 50', 50" or 94 provides a supportive backdrop for at least half of this distance. It should be noted that the entire pledget 74, 74', 74" or 75 can provide a supportive backdrop even though the bulge 76, 76', 76" or 96 provides the greatest amount of support. The actual distance over which the bulge 76, 76', 76" or 96 extents can be adjusted so that it alone will provide the entire supportive backdrop, see FIG. 11.

Referring to FIG. 18, the method further includes removing or withdrawing the urinary incontinence device 50, 50', 50" or 94 from the vagina 12.

As mentioned above with reference to the urinary incontinence device 50, 50', 50" or 94, the pledget 74, 74', 74" or 75 can be housed in an applicator 78 prior to use. The applicator 78 will assist in providing a comfortable insertion as well as retaining the urinary incontinence device 50, 50', 50" or 94 in a compressed state until it is ready for use. Once the urinary incontinence device 50, 50', 50" or 94 is removed from the applicator 78, it can be inserted into a woman's vagina 12. The first absorbent 58 and the second absorbent 64, 64' or 64" are capable of expanding upon absorbing moisture and/or body fluid while being positioned in the vaginal canal 26. The pledget 74, 74', 74" or 75 should be designed to be able to expand at least about 25% in the radial direction upon absorbing body fluid. Preferably, the pledget 74, 74', 74" or 75 should be designed to be able to expand at least about 50% in the radial direction upon absorbing body fluid. Most preferably, the pledget 74, 74', 74" or 75 should be designed to be able to expand at least about 100% in the radial direction upon absorbing body fluid. This expansion is measured starting from the initial diameter or width $W_2$ of the compressed pledget 74, 74', 74" or 75.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

I claim:

1. A urinary incontinence device comprising:
   a) a first absorbent having a width; and
   b) a second absorbent positioned adjacent to said first absorbent, said second absorbent having a width that is less than about 80% of the width of said first absorbent, said first and second absorbents being formed into a softwind that is compressed into an elongated pledget having a cross-sectional area, said first and second absorbents capable of absorbing fluid and expanding said cross-sectional area of said pledget, and said second absorbent causing a portion of said cross-sectional area of said pledget to expand farther outward to provide a supportive backdrop for a woman's urethra when inserted into a woman's vagina.

2. The urinary incontinence device of claim 1 wherein said compressed pledget has an insertion end, a trailing end and a uniform cross-sectional area extending between said ends, and after absorbing body fluid, said pledget exhibits a non-uniform cross-sectional area.

3. The urinary incontinence device of claim 1 wherein as said pledget absorbs fluid, said second absorbent will extend a portion of said cross-sectional area of said pledget outward at least 10% more than the expansion of said cross-sectional area by said first absorbent.

4. The urinary incontinence device of claim 3 wherein said second absorbent has an absorbent capacity which is at least equal to the absorbent capacity of said first absorbent measured in grams/grams.

5. The urinary incontinence device of claim 3 wherein said second absorbent has an absorbent capacity which is less than the absorbent capacity of said first absorbent measured in grams/grams.

6. The urinary incontinence device of claim 1 wherein said first absorbent has a longitudinal axis and said first and second absorbents are folded perpendicularly to said longitudinal axis to form said softwind.

7. The urinary incontinence device of claim 1 wherein said first absorbent has a longitudinal axis and said first and second absorbents are radially wound along said longitudinal axis to form said softwind.

8. The urinary incontinence device of claim 1 wherein said second absorbent has a width that is less than about 50% of the width of said first absorbent.

9. The urinary incontinence device of claim 8 wherein said second absorbent has a width that is less than about 35% of the width of said first absorbent.

10. A urinary incontinence device comprising:
    a) a first elongated absorbent having a width;
    b) a second absorbent positioned adjacent to said first absorbent, said second absorbent having a width that is less than about 50% of the width of said first absorbent, said first and second absorbents being radially wound into a softwind that is compressed into an elongated pledget having a uniform cross-sectional area, said first and second absorbents capable of absorbing body fluid and expanding said cross-sectional area of said pledget, and said second absorbent causing a portion of said cross-sectional area of said pledget to expand farther outward to provide a supportive backdrop for a woman's urethra when inserted into a woman's vagina; and
    c) withdrawal means for removing said urinary incontinence device from a woman's vagina.

11. The urinary incontinence device of claim 10 wherein as said pledget absorbs fluid, said second absorbent will extend a portion of said cross-sectional area of said pledget outward at least 10% more than the expansion of said cross-sectional area by said first absorbent.

12. The urinary incontinence device of claim 10 said compressed pledget has an insertion end, a trailing end and a uniform cross-sectional area extending between said ends, and after absorbing body fluid, said pledget exhibits a non-uniform cross-sectional area.

13. The urinary incontinence device of claim 12 further comprising a cover that at least partially encloses said pledget, said cover being an elongated member positioned adjacent to said first absorbent and extending from approximately said insertion end to approximately said trailing end, and said cover being treated with a surfactant to render a first zone located adjacent to said insertion end and a second zone located adjacent to said trailing end hydrophobic.

14. The urinary incontinence device of claim 13 wherein said cover has a third zone located between said first and second zones and said third zone is hydrophilic.

15. The urinary incontinence device of claim 14 wherein said third zone of said cover has a width and said second absorbent has a width, and said width of said third zone is approximately equal to said width of said second absorbent.

16. A urinary incontinence device comprising:
    a) a first elongated absorbent having a width and a longitudinal axis;
    b) a second absorbent positioned adjacent to said first absorbent and aligned along said longitudinal axis, said second absorbent having a width that is less than about 35% of the width of said first absorbent, said first and second absorbents being radially wound along said longitudinal axis into a softwind that is compressed into an elongated pledget having a uniform cross-sectional area, said first and second absorbents capable of absorbing fluid and expanding said cross-sectional area of said pledget, and said second absorbent causing a portion of said cross-sectional area of said pledget to expand radially outward by at least 10% more than the expansion of those portions containing just said first absorbent to provide a supportive backdrop for a woman's urethra when inserted into a woman's vagina;
    c) a cover at least partially enclosing said pledget; and
    d) withdrawal means for removing said urinary incontinence device from a woman's vagina.

17. The urinary incontinence device of claim 16 wherein said withdrawal means is a withdrawal string.

18. The urinary incontinence device of claim 17 wherein an aperture is formed through said first absorbent and said withdrawal string passes through said aperture.

19. The urinary incontinence device of claim 16 wherein said pledget has an insertion end and a trailing end and said cover is positioned adjacent to said first absorbent and extend from approximately said insertion end to approximately said trailing end, and said cover being treated with a surfactant to render a first zone located adjacent to said insertion end and a second zone located adjacent to said trailing end hydrophobic.

20. The urinary incontinence device of claim 19 wherein said cover has a third zone located between said first and second zones and said third zone is hydrophilic.

* * * * *